United States Patent [19]

Fabricius et al.

[11] Patent Number: 5,691,129
[45] Date of Patent: Nov. 25, 1997

[54] ZEROMETHINE MEROCYANINE DYES USEFUL AS SPECTRAL SENSITIZERS IN PHOTOGRAPHIC ELEMENTS

[75] Inventors: Dietrich Max Fabricius, Hendersonville, N.C.; Ralf Hermann Harms, Neu-Isenburg, Germany; James Joseph Welter, Flat Rock, N.C.

[73] Assignee: Sterling Diagnostic Imaging, Inc., Glasgow, Del.

[21] Appl. No.: 747,411

[22] Filed: Nov. 12, 1996

Related U.S. Application Data

[62] Division of Ser. No. 612,354, Mar. 7, 1996, Pat. No. 5,587,482.

[51] Int. Cl.$^6$ .................................................. G03C 1/10
[52] U.S. Cl. ......................... 430/578; 430/591; 430/502; 430/966
[58] Field of Search ................................ 430/591, 572, 430/578, 502

[56] References Cited

U.S. PATENT DOCUMENTS

| | | | |
|---|---|---|---|
| 2,256,163 | 9/1941 | Kumetat et al. | 95/7 |
| 2,354,524 | 7/1944 | Kumetat et al. | 260/240 |
| 3,655,393 | 4/1972 | Van Lare et al. | 430/591 |
| 3,734,739 | 5/1973 | Borror . | |
| 3,796,580 | 3/1974 | Ohlschlager et al. . | |
| 3,909,274 | 9/1975 | Beretta et al. . | |
| 4,028,353 | 6/1977 | Borror | 430/588 |
| 4,057,430 | 11/1977 | Sato et al. . | |
| 5,108,887 | 4/1992 | Fabricius et al. | 430/591 |
| 5,229,262 | 7/1993 | Arai et al. | 430/583 |
| 5,276,928 | 1/1994 | Fabricius | 430/594 |

OTHER PUBLICATIONS

CA111:87274z Novel Sensitizer Dye using Silver Halide Photographic Material, Onda et al., p. 632, 1989.

*Primary Examiner*—Richard L. Schilling
*Attorney, Agent, or Firm*—Joeseph T. Guy, Jr.

[57] ABSTRACT

The present invention is directed to a dye suitable for spectral sensitization of a photographic element. Specifically, the dye is a compound having the structure:

wherein:

$R^1$, $R^2$, $R^3$, and $R^4$ each independently represents H; halogen; alkyl of 1–6 carbons; aryl of 6–24 carbons; alkoxy of 1–6 carbons; carbonyl; or sulfonate; or $R^1$ and $R^2$, $R^2$ and $R^3$, or $R^3$ and $R^4$ taken together represent the atoms necessary to complete a six-membered carbocylic ring;

$R^5$ represents hydrogen, alkyl of 1–6 carbons or aryl of 6–24 carbons;

$R^6$, $R^7$, and $R^8$ independently represent alkyl 1–6 carbons; aryl of 6–24 carbons; or any pair of $R^6$, $R^7$ and $R^8$ taken together represent a five- or six-member heterocyclic ring;

X represents O, S, CH=CH, Se, Te or N—$R^{10}$;

Y represents O, S, or N—$R^9$;

Z represents O, S or Se;

$R^9$ represents alkyl of 1–6 carbons; or an aryl of 6–24 carbons;

$R^{10}$ represents alkyl of 1–6 carbons;

n is an integer of 1–6; and

Q represents a counterion.

12 Claims, No Drawings

ZEROMETHINE MEROCYANINE DYES USEFUL AS SPECTRAL SENSITIZERS IN PHOTOGRAPHIC ELEMENTS

This is a division of application Ser. No. 08/612,354, filed Mar. 6, 1996, now U.S. Pat. No. 5,587,482.

FIELD OF INVENTION

The present invention is related to a novel zeromethine merocyanine dye. More specifically, the present invention is related to a novel zeromethine merocyanine dye which has utility as a spectral sensitizing dye for photographic elements.

BACKGROUND OF THE INVENTION

Silver halide photographic emulsions are well known in the art. It is known in the art that silver halide emulsions can be spectrally sensitized to increase the photographic response to specific wavelengths of actinic radiation.

Spectral sensitization of photographic emulsions to blue and ultra-violet radiation is a widely recognized desire in the art. This desire is due, in part, to the superior resolution which can be obtained in blue and ultraviolet sensitive medical X-ray films relative to green or red sensitive medical X-ray films.

Zeromethine merocyanine dyes have been shown to be effective for spectral sensitization of tabular grains to blue light as detailed in U.S. Pat. No. 5,108,887. The compounds taught employ the methyl derivative at the benzothiazole nitrogen. Replacing the methyl group of the benzothiazole nitrogen with an ethyl or sulfobutyl group was shown to be detrimental to the function of the dye. Furthermore, the dyes of U.S. Pat. No. 5,108,887 are only effective for tabular grains and not for other important grain morphologies such as cubic. Based on the teachings of U.S. Pat. No. 5,108,887 a skilled artisan was led to the conclusion that the methyl substituent was critical and that substitution thereof was not advantageous.

The dye art is replete with teachings on the similarities of dye substituents. U.S. Pat. No. 4,028,355, for example, indicates the equivalency of alkyl ammonium, alkyl sulfonate, and alkyl phosphonate on trimethine dyes. The similarities do not translate to zeromethine dyes as indicated by the marked difference between methyl and ethyl substitution and the inapplicability of the butyl sulfonate as taught in U.S. Pat. No. 5,108,887.

Described herein is a novel zeromethine merocyanine dye comprising an alkyl ammonium substituent which surprisingly renders the dye suitable as a spectral sensitizer for silver halide photographic elements. This novel dye provides adequate photographic response at a low level of fog and without the appearance of staining due to residual dye remaining in the film element after photographic processing. Furthermore, the dye is suitable for spectral senstization to both blue and ultraviolet light and for use with various grain morphologies.

SUMMARY OF THE INVENTION

It is an object of the present invention to provide a dye which is suitable for spectral sensitization of silver halide photographic elements.

It is a particular object of the invention to provide a dye which is suitable for sensitizing a silver halide photographic element to blue and UV radiation without the deterimental effects of fog and dye staining.

It is yet another object of the present invention to provide a dye which is suitable for spectral sensitization of silver halide grains of both tabular and cubic morphology.

These and other advantages, as will be apparant from the teachings herein, are provided in a compound having the structure:

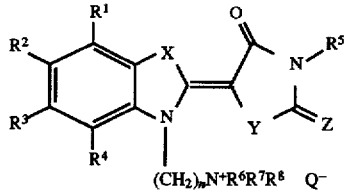

wherein:

$R^1$, $R^2$, $R^3$, and $R^4$ each independently represents H; halogen; alkyl of 1–6 carbons; aryl of 6–24 carbons; alkoxy of 1–6 carbons; carbonyl; or sulfonate; or $R^1$ and $R^2$, $R^2$ and $R^3$, or $R^3$ and $R^4$ taken together represent the atoms necessary to complete a six-membered carbocyclic ring;

R5 represents hydrogen, alkyl of 1–6 carbons or aryl of 6–24 carbons;

$R^6$, $R^7$, and R8 independently represent alkyl 1–6 carbons; aryl of 6–24 carbons; or any pair of $R^6$, $R^7$ and $R^8$ taken together represent a five- or six-member heterocyclic ring;

X represents O, S, CH=CH, Se, Te or N—$R^{10}$;

Y represents O, S, or N—$R^9$;

Z represents O, S or Se;

$R^9$ represents alkyl of 1–6 carbons; or an aryl of 6–24 carbons;

$R^{10}$ represents alkyl of 1–6 carbons;

n is an integer of 1–6; and

Q represents a counterion.

A particularly preferred embodiment of the present invention is a photographic element comprising a support with at least one hydrophilic colloid layer coated thereon; said hydrophilic colloid layer comprises silver halide grains which are spectrally sensitized with at least one dye represented by

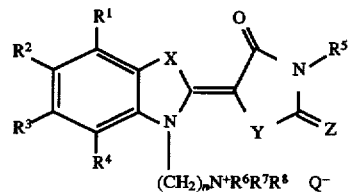

wherein $R^1$, $R^2$, $R^3$, and $R^4$ each independently represents H; halogen; alkyl of 1–6 carbons; aryl of 6–24 carbons; alkoxy of 1–6 carbons; carbonyl; or sulfonate; or $R^1$ and $R^2$, $R^2$ and $R^3$, or $R^3$ and $R^4$ taken together represent the atoms necessary to complete a six-membered carbocyclic ring;

$R^5$ represents hydrogen, alkyl of 1–6 carbons or aryl of 6–24 carbons;

$R^6$, $R^7$, and $R^8$ independently represent alkyl 1–6 carbons; aryl of 6–24 carbons; or any pair of $R^6$, $R^7$ and $R^8$ taken together represent a five- or six-member heterocyclic ring;

X represents O, S, CH=CH, Se, Te or N—R¹⁰;

Y represents O, S, or N—R⁹;

Z represents O, S or Se;

R⁹ represents alkyl of 1–6 carbons; or an aryl of 6–24 carbons;

R¹⁰ represents alkyl of 1–6 carbons;

n is an integer of 1–6; and

Q represents a counterion.

DETAILED DESCRIPTION OF THE INVENTION

The dye of the present invention is exemplified by Formula I.

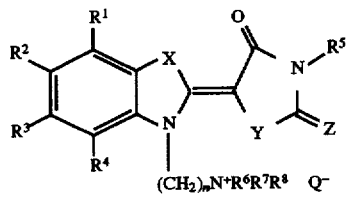

Formula 1

In Formula 1, $R^1$, $R^2$, $R^3$, and $R^4$ each independently represents H; halogen; alkyl, or substituted alkyl, of 1–6 carbons; aryl, or substituted aryl, of 6–24 carbons; alkoxy of 1–6 carbons; carbonyl; or sulfonate. Alternatively, $R^1$ and $R^2$, $R^2$ and $R^3$, or $R^3$ and $R^4$ taken together represent the atoms necessary to complete a six-membered carbocylic ring or a substituted six-membered carbocylic ring. Preferably, $R^1$, $R^2$, $R^3$, and $R^4$ each independently represents H; halogen; alkyl, or substituted alkyl, of 1–6 carbons; alkoxy of 1–6 carbons; carbonyl; or sulfonate; or $R^1$ and $R^2$, $R^2$ and $R^3$, or $R^3$ and $R^4$ taken together represent the atoms necessary to complete a naphthyl ring.

$R^5$ represents alkyl, or substituted alkyl, of 1–6 carbons; or aryl, or substituted aryl, of 6–24 carbons.

$R^6$, $R^7$, and $R^8$ independently represent alkyl, or substituted alkyl of 1–6 carbons; aryl, or substituted aryl, of 6–24 carbons; or any pair of $R^6$, $R^7$ and $R^8$ can be taken together to form a five- or six-member heterocyclic ring or a substituted five- or six-member heterocyclic ring. Preferably, $R^6$, $R^7$ and $R^8$ independently represent alkyl, or substituted alkyl, of 1–6 carbons.

X represents O, S, CH=CH, Se, Te or N—R¹⁰. Preferably, X represents O, S, CH=CH or NR¹⁰. More preferably, X represents O, S, or NR¹⁰. Most preferably, X represents O or S.

Y represents O, S, or N—R⁹. Preferably, Y represents O or S. Most preferably, Y represents S.

Z represents O, S or Se. Preferably, Z represents O or S. Most preferably, Z represents S.

$R^9$ represents alkyl, or substituted alkyl, of 1–6 carbons, or an aryl, or substituted aryl, of 6–24 carbons. Preferably, $R^9$ represents alkyl, or substituted alkyl, of 1–6 carbons.

$R^{10}$ represents alkyl, or substituted alkyl, of 1–6 carbons.

n is an integer of 1–6. Preferably, n is an integer from 2–4. Most preferably, n is the integer 3.

Q⁻ represents a counterion, as necessary, to balance the charge. The counterion is chosen for convenience since the counterion has mainly secondary effects on the properties of the dye when used as a spectral sensitizer in photographic elements. Preferred counterions include, but are not limited to, Cl, Br, I, p-toluenesulfonate, tetraphenyl borate, tetrafluoroborate, CF₃SO₃—, and SF₆—. Particularly preferred counterions include, Cl, Br, I and p-toluenesulfonate. The most preferred counterion is bromide.

Particularly exemplary dyes are represented by the following list which is intended to illustrate, not limit, the invention.

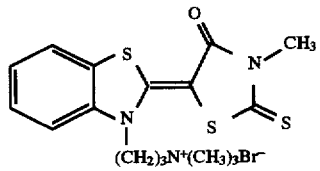

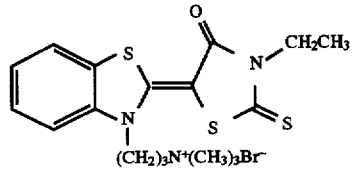

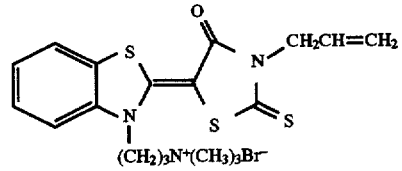

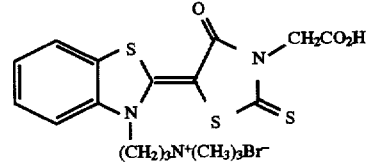

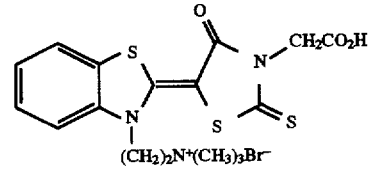

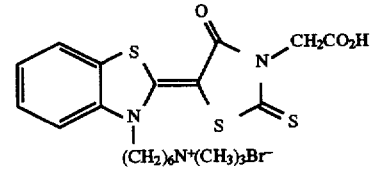

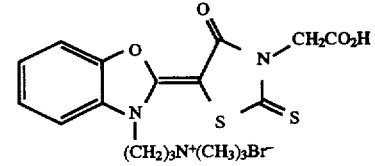

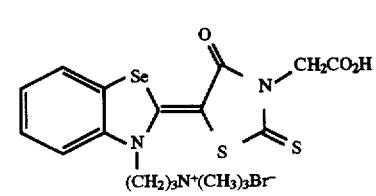

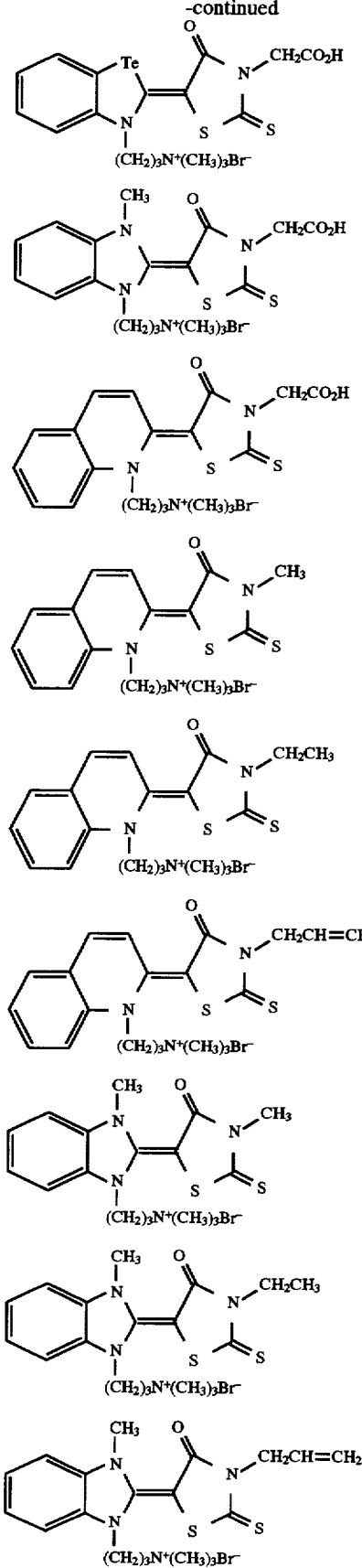
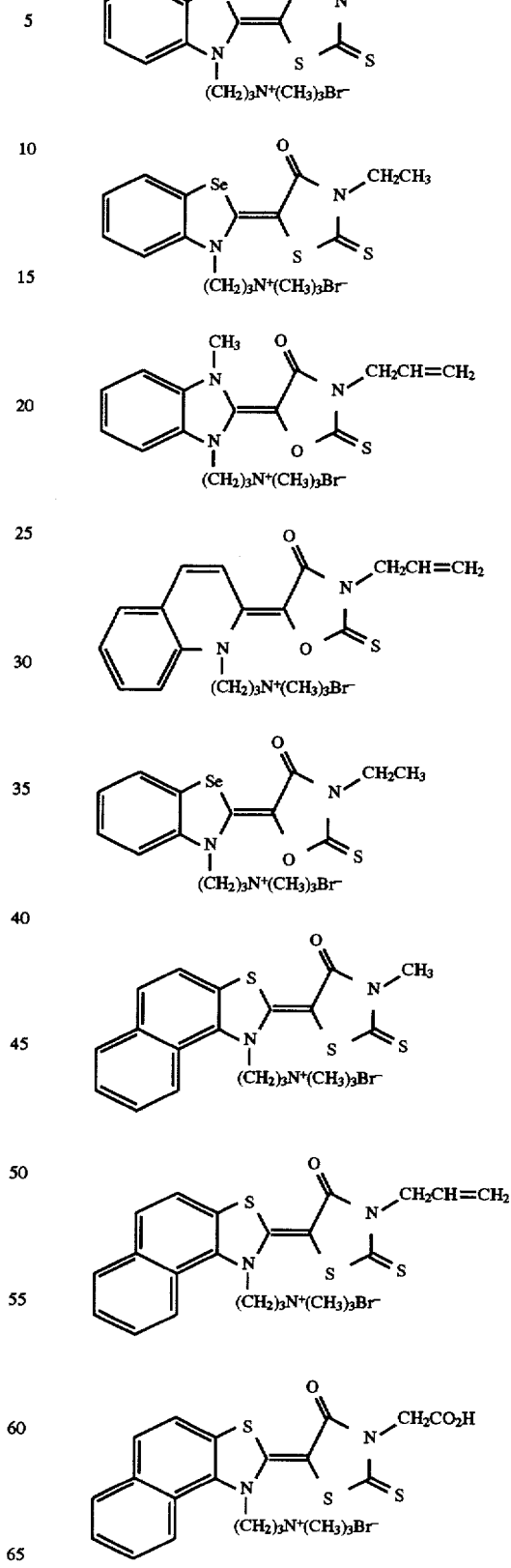

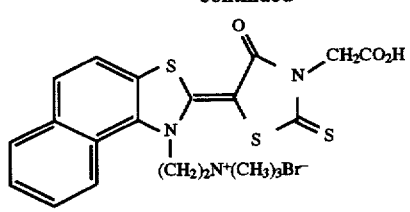
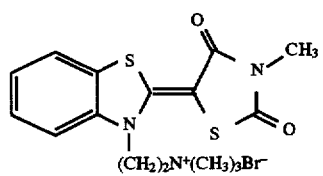
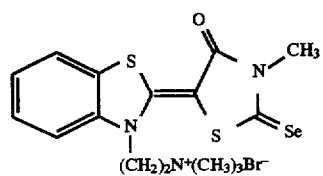
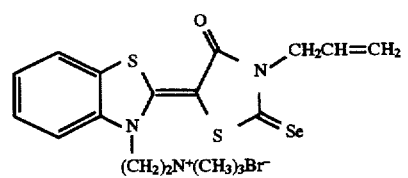
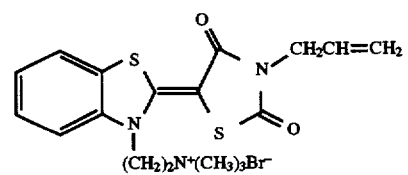
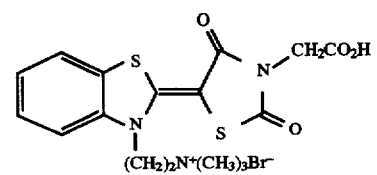
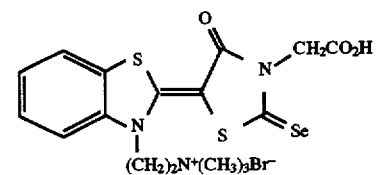
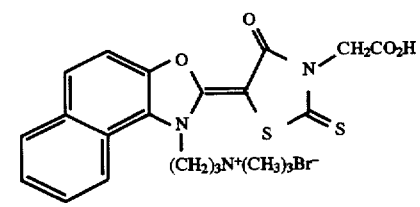
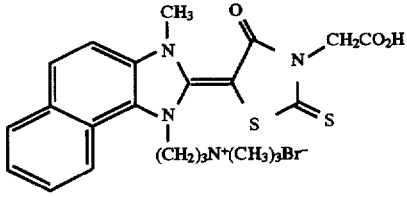
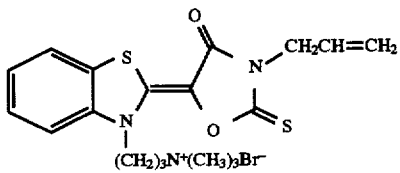
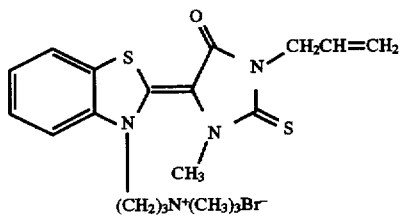
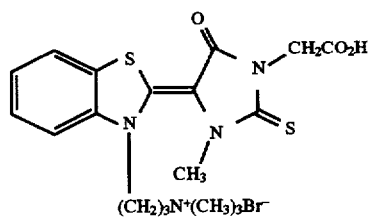
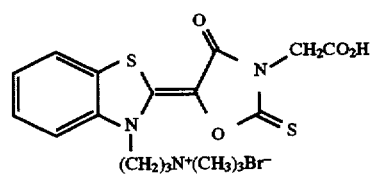
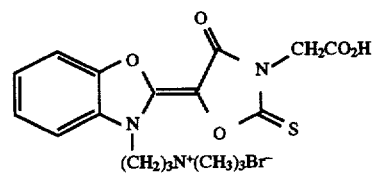
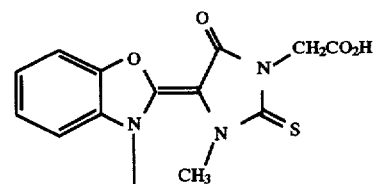
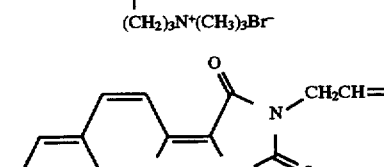
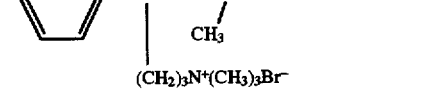

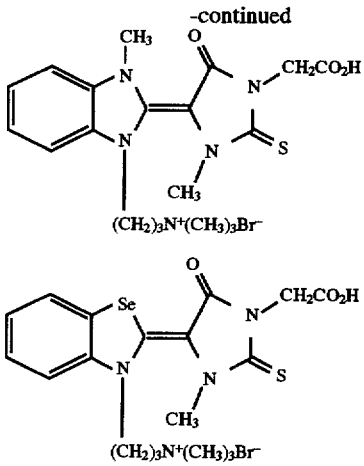

Throughout the specification the orientation of the rings about the central alkene is drawn for convenience and is not limiting. A skilled artisan would appreciate that alternate orientations are within the scope of the invention.

The terms "alkyl", "aryl", and "aralkyl" and other groups refer to both unsubstituted and substituted groups unless specified to the contrary. Alkyl can be saturated, unsaturated, straight chain or branched and unless otherwise specified refers to alkyls of 1 to 24 carbon atoms. Unless otherwise specified the term aryl refers to aryl of 6 to 24 carbons and the term aralkyl refers to aralkyl of 7 to 25 carbons. Preferred substituents include but are not limited to halogen; nitro; carboxyl in the form of a salt or carboxylic acid; hydroxyl; alkoxy; amine; thiol; amide; vinyl; sulfate; cyano; alkylammonium, carbonyl and thioether.

The term "carbocyclic ring" refers specifically to unsubstituted and substituted aromatic carbon rings such as phenyl, napthyl, etc. wherein 5 or 6 membered carbon rings are either used alone or fused together. Carbocyclic ring substituents include halogen; nitro; carboxyl in the form of a salt or carboxylic acid; hydroxyl; alkoxy; amine; thiol; amide; vinyl; sulfate; cyano; alkylamnmonium, carbonyl and thioether. The term five- or six member heterocyclic ring refers to the atoms chosen from C, N, O, and S necessary to form a ring. Specifically preferred examples include phenyl, pyridine, pyrimidine, pyrazine, cyclopentane, cyclopentene, cyclohexane, cyclohexene, furan, pyran, pyrrole, pyrroline, pyrrolidine, piperidine, piperizine and pyridazine. The term aromatic 10-membered ring refers to the atoms chosen from C, N, O and S necessary to form an aromatic 10-membered ring. Specific examples include quinoline, naphthalene, phthalazine, naphthyridine, quinoxaline, quinazoline, cinnoline and pteridine.

The dyes of this invention may be dissolved in any of a host of suitable solvents including methanol, ethanol, water or dilute aqueous sodium hydroxide. The dyes of the present invention are useful for a myriad of applications known to the art. While not specifically limited thereto the preferred use is as a spectral sensitizer in photographic silver halide films elements.

When used as a sensitizing dye in a silver halide photographic element the dyes can be added as a concentrated slurry in the aforementioned solvents or more preferably as a solution. Time of addition is typically not critical. The dyes can be added at any time during the preparation of the silver halide grains, prior to or after the addition of gold and sulfur salts or after chemical sensitization is complete. Most preferable is addition during chemical sensitization. The amount of dye added is preferably 10 to 5000 mg of dye per mole of silver and preferably from 20 to 2000 mg of dye per mole of silver.

Any of the conventional halides may be used but preferred is pure silver bromide or silver bromide with up to 5% iodide, by weight, incorporated therein. A silver halide grain with 98% Br and 2% I, by weight, is suitable for demonstration of the utility of the inventive dyes of the present invention. Any grain morphology is suitable for demonstration of these teachings including, but not limited to, grains which are formed by splash techniques and those formed by spray techniques. Tabular grains are most preferred.

The grains are preferably dispersed in a binder (e.g. gelatin or other well-known binders such as polyvinyl alcohol, phthalated gelatins, etc.). In place of gelatin other natural or synthetic water-permeable organic colloid binding agents known in the art can be used as a total or partial replacement thereof. It is common to use binder adjuvants useful for increasing covering power such as dextran or the modified, hydrolysed gelatins of Rakoczy, U.S. Pat. No. 3,778,278.

It is most preferable to chemically sensitize the grain with salts that are well known in the art. The most common sensitizers are salts of gold or sulfur. Sulfur sensitizers include those which contain labile sulfur, e.g. allyl isothiocyanate, allyl diethyl thiourea, phenyl isothiocyanate and sodium thiosulfate for example. The polyoxyalkylene ethers in Blake et al., U.S. Pat. No. 2,400,532, and the polyglycols disclosed in Blake et al., U.S. Pat. No. 2,423,549. Other non-optical sensitizers such as amines as taught by Staud et al., U.S. Pat. No. 1,925,508 and Chambers et al., U.S. Pat. No. 3,026,203, and metal salts as taught by Baldsiefen, U.S. Pat. No. 2,540,086 may also be used. Additional spectral sensitizing dyes may be used. The methods are well known in the art and include, but are not limited to, cyanines, merocyanines, oxonols, hemioxonols, styryls, merostyryls, complex cyanines and merocyanines (i.e. tri-, tetra-, and polynuclear cyanines and merocyanines), and streptocyanines as illustrated in *Research Disclosure*, No 308, December, 1989, Item 308119.

The emulsions can contain known antifoggants, e.g. 6-nitrobenzimidazole, benzotriazole, triazaindenes, etc., as well as the usual hardeners, i.e., chrome alum, formaldehyde, dimethylol urea, mucochloric acid, etc. Other emulsion adjuvants that may be added comprise matting agents, plasticizers, toners, optical brightening agents, surfactants, image color modifiers, non-halation dyes, and covering power adjuvants among others.

The film support for the emulsion layers used in the novel process may be any suitable transparent plastic. For example, the cellulosic supports, e.g. cellulose acetate, cellulose triacetate, cellulose mixed esters, etc. may be used. Polymerized vinyl compounds, e.g., copolymerized vinyl acetate and vinyl chloride, polystyrene, and polymerized acrylates may also be mentioned.

When polyethylene terephthalate is manufactured for use as a photographic support, it is preferable to use a mixed polymer subbing composition such as that taught by Rawlins, U.S. Pat. No. 3,567,452, Miller, U.S. Pat. Nos. 4,916,011 and 4,701,403, Cho, U.S. Pat. Nos. 4,891,308 and 4,585,730 and Schadt, U.S. Pat. No. 4,225,665. Upon completion of stretching and application of subbing composition, it is necessary to remove strain and tension in the base by a heat treatment comparable to the annealing of glass.

The emulsions may be coated on the supports mentioned above as a single layer or multi-layer element. For medical x-ray applications, for example, layers may be coated on both sides of the support which conventionally contains a dye to impart a blue tint thereto. Contigous to the emulsion layers it is conventional, and preferable, to apply a thin stratum of hardened gelatin supra to said emulsion to provide protection thereto.

The emulsions of this invention can be used in any of the conventional photographic systems (e.g. negative or positive-working systems). Thus, they can contain any of the adjuvants related to the particular system employed. For example, the emulsions when employed as direct positive may be chemically fogged using metals such as rhodium or iridium and the like, or with other chemical fogging agents such as boranes, as well-known to those skilled in the art.

It is conventional to use the photographic emulsions of this invention with X-ray intensifying screens. These are usually used in pairs in cooperation with double-side coated medical X-ray silver halide photographic film elements, although it is sometimes common to use single-side coated silver halide photographic film elements for some applications. A pair of screens is conventionally used and the coating weights of each screen may be different, if required. Thus, an asymmetric pair of screens can be used to get the best results. Medical X-ray evaluations represent a commercial use for the photographic element comprising the inventive dye. The application is typically exposed by a phosphor cast into an X-ray intensifying screen.

Although any conventional silver halide photographic system can be employed to demonstrate the teachings of this invention a medical radiographic system will be used as an illustrative example.

EXAMPLES

Dye preparation procedures are exemplified by the method set forth for Dyes 1–5 of Table 1. Inventive dyes can be prepared in analogous manner using standard organic synthetic preparative techniques well known to the art.

TABLE 1

| X | R$^5$ | $^1$Max$^{nm}$(ex 10$^{-4}$) | mp(°C.) |
|---|---|---|---|
| Dye 1 | S | CH$_2$CO$_2$H | 424(6.1) | 285–86 |
| Dye 2 | S | CH$_3$ | 424(6.1) | 278–79 |
| Dye 3 | S | CH$_2$CH$_3$ | 426(7.5) | 245–48 |
| Dye 4 | S | CH$_2$CH=CH$_2$ | 425(8.4) | 255–57 |
| Dye 5 | NCH$_3$ | CH$_2$CO$_2$H | 412 | |

PREPARATION OF DYE INTERMEDIATES 3-(Bromopropyl)trimethylammonium bromide (Int-A).

Trimethylamine (21.1 ml) was condensed at −78° C. (dry ice/isopropanol) and added to stirred and ice-cooled 1,3-dibromopropane (56.65 gm, 0.266 mol) in 135 ml toluene. The solution hazed immediately, but was allowed to stir 2.5 days. The white precipitate was collected by filtration to yield 63.34 gm, which was dried by vacuum to give 51.36 gm (87%), mp. 203°–207° C. (dec.)

2-(3-Trimethylammoniumpropylthio)benzothiazole bromide (Int-B).

Potassium hydroxide (56 gm, 1 mol) was added to a slurry of 2-mercaptobenzothiazole (167 gm, 1 mol) in 600 ml 95% ethanol to give a dark solution. 3-(Bromopropyl) trimethylammonium bromide (Int-A) (261 gm, 1 mol) was added and the mixture heated to reflux liar 55 min. Upon cooling, potassium bromide precipitated and was removed by filtration. The filtrate was evaporated and the residue recrystallized from isopropanol to obtain 182.52 gm, mp 167°–170° C. An additional 97.86 gm was obtained from concentration of the filtrate.

2-(3-Trimethylammoniumpropylthio)-3-(3 trimethyl ammoniumpropyl)-benzothiazole dibromide (Int-C).

2-(3-Trimethyl ammoniumpropylthio)-benzothiazole bromide (Int-B) (86.30 gm, 0.248 mol) and 68.53 gm (0.26 mol) 3-(Bromopropyl)trimethyl ammonium bromide were heated together with mechanical stirring at 133°–147° C. in an 156° C. oil bath for 5 hours. The product was cooled to 89° C. before adding 200 ml methanol to give a black solution. The solution was filtered prior to use in subsequent dye condensations.

2-Methylthio-1-(3-Trimethylammoniumpropylthio) benzimidazolium bromide (Int-D).

2-Methylthiobenzimidazole (8.2 gm, 0.05 mol., from Aldrich Chemical Co.) was slurried in 50 ml dry THF. 60% NaH (2.0 g) was washed with o-xylene and added as a slurry to previous mixture. After considerable gas evolution, the mixture nearly cleared to a brown solution. Trimethylammoniumpropyl bromide (13.05 gm, 0.05 mol) was added and resulting mixture stirred at room temperature overnight. The mixture was filtered and the recovered hygroscopic white solid was washed several times with acetone and then vacuum-dried to yield 9.84 gm (57% yield), mp 175° C. (dec). C$^{13}$ NMR was satisfactory.

1-Methyl-2-Methylthio-3-(3 Trimethylammoniumpropylthio) benzimidazolium bromotosylate (Int-E).

Int-D (3.44 gm, 0.01 mol), methyl rosylate (2.0 gm, 0.01 mol) and 20 ml o-xylene were mixed together and heated to reflux. After five hours, the mixture was cooled, mixed with acetone, and filtered to collect 4.50 gm, mp 250° C. (dec). NMR analysis revealed a purity of ~62% with 38% residual starting material. The entire product was refluxed with 6.0 gm methyl tosylate in 25 ml o-xylene for an additional 5 hours. Cooling and treatment with acetone yielded 2.96 gm product, mp>350° C.

EXEMPLARY PREPARATION TECHNIQUES FOR INVENTIVE DYES

Dye-1 2-[3-(3-Trimethylammoniumpropyl) benzothiazolylidene]-3-carboxymethyl-rhodanine bromide.

An equimolar amount of Int-C was mixed with 18.36 gm (0.096 mol) 3-carboxymethylrhodanine and 9.25 gm (0.092 mol) triethylamine. After stirring 24 hrs. at room temperature, the reaction mixture was filtered and washed with methanol to yield 2.92 gm green-yellow powder, mp 285°–286° C. I$_{max}$=424 nm (e=61,000). An additional 5.19 gm dye was obtained by allowing the filtrate to react longer.

Dye-2 2-[3-(3-Trimethylammoniumpropyl) benzothiazolylidene]-3-methylrhodanine bromide.

In a manner similar to the preparation of Dye-1, Int-C was reacted with 6.27 gm (0.043 mol) 3-methylrhodanine and 4.58 gm (0.045 mol) triethylamine. After six hours, the dye was collected by filtration and washed twice with 50 ml methanol to yield 5.81 gm (10.3%), mp 278°–279°C. I$_{max}$= 424 (e=61,000).

Dye-3 2-[3-(3-Trimethylammoniumpropyl) benzothiazolylidene]-3-ethylrhodanine bromide.

In a manner similar to the preparation of Dye-1, Int-C was reacted with 6.60 gm (0.041 mol) 3-ethylrhodanine and 4.14 gm (0.041 mol) triethylamine. After 24 hours, a small amount of dye was collected by filtration. The filtrate was evaporated and the residue treated with 20 ml conc. HCl and 1000 ml water. The aqueous phase was decanted away from the resulting oil, further diluted with 2000 ml water and treated with aq. KOH to precipitate the dye. After filtering and washing with methanol, the yield was 1.14 g, mp 245°–248° C. $I_{max}$425 (e=75,000).

Dye-4 2-[3-(3-Trimethylammoniumpropyl) benzothiazolylidene]-3-allylrhodanine bromide.

In a manner similar to the preparation of Dye-1, Int-C was reacted with 4.69 gm (0.027 mol) 3-allylrhodanine and 2.73 gm (0.027 mol) triethylamine. After five hours, the dye was collected by filtration and washed twice with 50 ml methanol to yield 5.17 gm (8.7%), mp 255°–257° C. $I_{max}$=425 (e=84,000).

Dye-5 2-[1-Methyl-3-(3-trimethylammoniumpropyl) benzimidazolylidene]-3-carboxymethyl-rhodanine bromide.

Int-E (2.96 gm, 0.0048 mol), 3-carboxymethylrhodanine (0.91 gm, 0.0048 mol), 10 ml dimethylformamide, and triethylamine (0.96 gm 0.0096 mol) were stirred together at room temperature for five hours. The mixture was filtered, the filtrate acidified with conc. HCl, and diluted with isopropanol to precipitate tosylate salts. The precipitant was removed by filtration and filtrate rotary evaporated to remove all solvent. The residue was treated with acetone and the precipitated triethylammonium salts removed by filtration. The acetone solution was concentrated by rotary evaporation and then poured into ethyl acetate to precipitate a yellow oil. The solvent was decanted away, the oil dissolved in isopropanol, and then poured into ethyl acetate to precipitate a gum. The solvent was decanted away, the oil dissolved in methanol/isopropanol, and then poured into ethyl acetate to precipitate a yellow solid, 0.06 gm, $I_{max}$=412 nm.

Other inventive dyes can be prepared in a manner analogous to the exemplary procedures detailed above. The substituted rhodanine can be substituted with oxazolidinone or thiohydantoin to form the dye derivatives with Y being O or $NR^{16}$. Substituting a thioxo-4-oxazolidinone for rhodanine can be used to synthesize the dye derivatives with Z being oxygen. Inventive dyes with Z being Se can be prepared in a manner analogous to that taught in U.S. Pat. No. 2,332,433. The substituted benzothiazole of the exemplary preparation examples can be replaced by appropriately substituted benzoxazole, benzselenazole, benztellurazole, quinoline or benzimidazole as necessary to form the dyes not specifically taught in the exemplary procedure. All of the preparation procedures use standard organic preparative techniques which are well known to the skilled artisan.

Screen Samples

Screen A is a standard LaOBr:Tm predominantly blue emitting screen which is commercially available from DuPont (Wihnington, Del.). Screen B is a standard $YTaO_4$:Nb predominantly blue emitting screen prepared as described in Brixner, U.S. Pat. No. 4,225,653 which is included herein by reference thereto. Screen C is a predominantly UV emitting $YTaO_4$ screen prepared by the procedure as described in Brixner and further elaborated below:

A. The Binder Solution:

The following ingredients were prepared:

| Ingredient | Amount (g) |
| --- | --- |
| n-Butyl acetate | 43.13 |
| n-Propanol | 34.00 |
| Carboset 525 (1) | 10.00 |
| Carboset 526 (2) | 10.00 |
| Polymeric organic silicone fluid | 0.07 |

-continued

| Ingredient | Amount (g) |
| --- | --- |
| Zelec 2457E (3) | 0.40 |
| Aerosol OT-100 (4) | 0.40 |
| Pluronic 31R1 (5) | 2.00 |

(1) Acrylic resin; ave. mol. wt. 260,000; acid no. 76–85; B.F. Goodrich Co., Cleveland, OH
(2) Acrylic resin; ave. mol. wt. 200,000; acid no. 100; B.F. Goodrich Co., Cleveland, OH
(3) Anionic antistatic agent of mixed mono and dialkylphosphates of the general structure R2HPO4, where R is C8 to C10 alkyl; E.I. du Pont de Nemours & Co., Wilmington, DE
(4) Sodium dioctyl sulfosuccinate per U.S. Pat. No. 2,441,341
(5) Ethylene oxide/propylene oxide block copolymer; ave. mol. wt. 3,200; BASF Wyandotte; Wyandotte, MI B. The X-ray Phosphor:

The following ingredients were thoroughly mixed in a paint shaker for about 2 hours before charging to a alumina crucible:

| Ingredient | Amount (g) |
| --- | --- |
| $Y_2O_3$ | 101.46 |
| $Ta_2O_5$ | 198.54 |
| $Li_2SO_4$ | 150.00 |

The crucible was then placed in a standard, commercial, high temperature furnace and fired at about 1200° C. for about 8 hours and then at about 1250° C. for about 16 hours. The furnace was then allowed to cool and the contents of the crucible weighed and washed thoroughly with water to remove the unreacted salts and flux. This material was then added to the binder from above using about 200 g of phosphor/60 gm of binder solution. This material was placed in a plastic container along with about 85 gm of 3.8 in. diameter corundum balls (ca. 15 balls) and this mixture was then ball milled for about 12 to 16 hours at room temperature with a rotation speed of about 60 rpm. After this step, the ball milled suspension was filtered through a 75 mesh Nylon bag and coated onto a suitable support.

The support used was 0.010 inch thick, dimensionally stable polyethylene terephthalate film containing a small amount of a whitener (e.g., anatase $TiO_2$) dispersed therein. This whitener will give the support some opacity to visible light (e.g. optical density of ca.>1.7). The coating weight of the phosphor dispersion placed thereon is about 100 mg of phosphor per $cm^2$.

C. The Overcoat Layer:

An overcoat layer is prepared from the following solutions:

| 1) Ingredient | Amount (gm) |
| --- | --- |
| Acetone | 67.00 |
| Methanol | 9.00 |
| n-Butyl acetate | 4.80 |
| Tyril* 100 (1) | 12.70 |
| Carboset* XL-27 (2) | 9.00 |

(1) Styrene/acrylonitrile copolymer resin; Dow Chemical Co., Midland, MI
(2) Acrylic resin; ave. mol. wt. 30,000; acid no. 80, B.F. Goodrich Co., Cleveland, OH A gel solution is prepared by mixing the following ingredients until a thick gel forms:

| 2) Ingredient | Amount (gm) |
| --- | --- |
| Methanol | 14.70 |
| Triamylamine | 0.20 |
| Carbopol* 1342(1) | 0.132 |

(1) Acrylic resin thickener; B.F. Goodrich Co., Cleveland, OH
This solution is filtered and a mixture is prepared as follows:

| 3) Ingredient | Amount (gm) |
| --- | --- |
| Solution 1 | 50.00 |
| Gel Solution 2 | 12.19 |

This mixture is coated on top of the phosphor coating using a doctor knife with a 0.004 in. gap. The resulting top-coat is air dried for 12–16 hrs. at 40° C.

PREPARATION OF PHOTOGRAPHIC EMULSION

Example 1

A silver bromide tabular grain emulsion was prepared according to the teachings of Ellis, U.S. Pat. No. 4,801,522. After precipitation of the grains the average aspect ratio was determined to be about 5:1 and thickness of about 0.21 μm. These grains were dispersed in photographic gelatin at about 117 grams gelation/mole of silver bromide. A suspension of 150 mg of Dye 1 in 75 ml methanol was added to achieve approximately 67 mg of dye per mole of silver halide. At this point, the emulsion was brought to its optimum sensitivity with gold and sulfur salts as is well-known to those skilled in the art. The emulsion was stabilized by the addition of 4-hydroxy-6-methyl-1,3,3a,7-tetraaza-indene and 1-phenyl-5-mercaptotetrazole. The usual wetting agents, antifoggants, coating aids, and hardeners were added and this emulsion was then coated on a dimensionally stable, 7 mil polyethylene terephthalate film support which had first been coated with a conventional resin sub followed by a thin substratum of hardened gelatin applied supra thereto. These subbing layers were present on both sides of the support. The emulsion was coated on one side at about 2 gm silver per square meter. A thin abrasion layer of hardened gelatin was applied over the emulsion layer. For control purposes, a similar emulsion was made without sensitizing dye. Samples of each of these coatings were given an X-ray exposure with Screen A using a conventional step wedge test target. The film was then developed in a conventional X-ray film processor. In all of the examples Rel. Speed is reported based on the control with the speed of the samples containing no dye being set to an arbitrary speed of 100. Fog is reported as net fog and does not include contributions from the support. The results of Example 1 are summarized in Table 2.

TABLE 2

| No. | Dye | Fog | Rel. Speed |
| --- | --- | --- | --- |
| 1 | Control - No dye | 0.07 | 100 |
| 2 | Dye 1 | 0.15 | 118 |

Example 2

An emulsion similar to that of Example 1 was prepared, except that comparative dyes A and B were added. All dyes were added at 0.33 mmol dye/mol silver bromide.

Comparitive DYE A

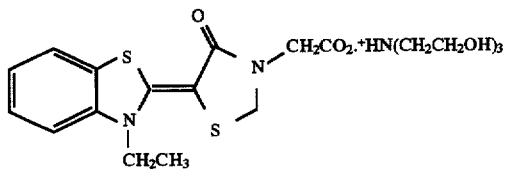

Comparitive DYE B

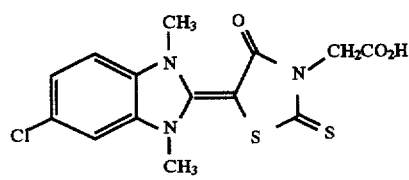

The photographic emulsion was tested under similar conditions as Example 1 using Screen A. Results from the evaluation of the samples of Example 2 are presented in Table 3.

TABLE 3

| No. | Dye | Rel. Speed |
| --- | --- | --- |
| 3 | Dye 1 | 118 |
| 4 | Comparative dye A | 91 |
| 5 | Comparative dye B | 91.5 |

Example 2 shows that comparative prior art dyes are not effective as spectral sensitizing dyes whereas the inventive dyes are effective.

Example 3

An emulsion similar to that of Example 1 was prepared, except that cubic silver halide grains were used and dyes C, D, and E were added in the amount each of 67 mg dye/mole silver bromide.

DYE C

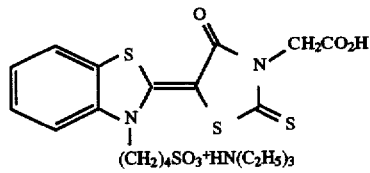

DYE D

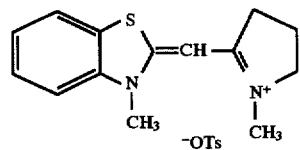

DYE E

-continued

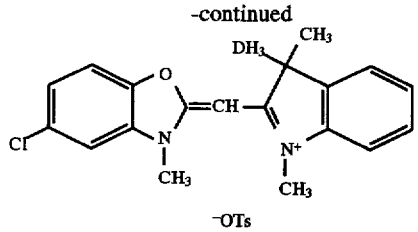
-OTs

The photographic emulsions were tested as a liquid using conventional techniques. Results of the evaluation are presented in Table 4.

TABLE 4

| Dye | Fog | Rel. Speed |
| --- | --- | --- |
| C | 0.05 | 98 |
| Dye 1 | 0.02 | 118 |
| D | 0.04 | 79 |
| E | 0.08 | 87.5 |

The results above clearly show that the inventive dyes offer improved spectral sensitization with cubic gains compared to a prior art merocyanine dye and to monomethine cyanine dyes. It is surprising to note that the sulfobutyl group decreases the speed relative to no dye (Speed=100) and that the inventive dyes increase photographic speed dramatically even at lower fog.

Example 4

An emulsion similar to that of Example 1 was prepared, except that comparative Dye F was added. All dyes were added at 0.50 mmol dye/mol silver bromide.

DYE F

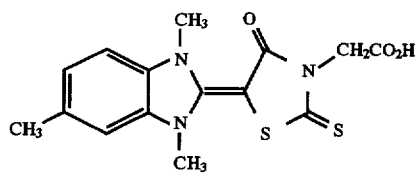

Evaluation of the samples gave the results presented in Table 5. The films were exposed with ultraviolet-emitting (Screen C) and blue-emitting (Screen B) X-ray phosphor screens.

TABLE 5

| Dye | Screen C | Screen B |
| --- | --- | --- |
| No dye | 100 | 100 |
| Dye 2 | 169 | 181 |
| Dye F | 80 | 72 |

These examples show that a comparative prior art dyes decrease the speed of the photographic emulsion relative to the control. The examples clearly illustrate the unexpected advantages as a spectral sensitizer for silver halide grains of different morphologies. Furthermore, the inventive dyes are suitable for sensitization to both blue and UV light with minimal fog.

We claim:

1. A photographic element comprising a support with at least one hydrophilic colloid layer coated thereon; said hydrophilic colloid layer comprises silver halide grains which are spectrally sensitized with at least one dye represented by

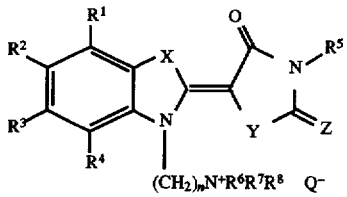

wherein $R^1$, $R^2$, $R^3$, and $R^4$ each independently represents H; halogen; alkyl of 1–6 carbons; aryl of 6–24 carbons; alkoxy of 1–6 carbons; carbonyl; or sulfonate; or $R^1$ and $R^2$, $R^2$ and $R^3$, or $R^3$ and $R^4$ taken together represent the atoms necessary to complete a six-membered carbocylic ring;

$R^5$ represents hydrogen, alkyl of 1–6 carbons or aryl of 6–24 carbons;

$R^6$, $R^7$, and $R^8$ independently represent alkyl 1–6 carbons; aryl of 6–24 carbons; or any pair of $R^6$, $R^7$ and $R^8$ taken together represent a five- or six-member heterocyclic ring;

X represents O, S, CH=CH, Se, Te or N—$R^{10}$;

Y represents O, S, or N—R9;

Z represents O, S or Se;

$R^9$ represents alkyl of 1–6 carbons; or an aryl of 6–24 carbons;

$R^{10}$ represents alkyl of 1–6 carbons;

n is an integer of 1–6; and

Q represents a counterion.

2. The photographic element recited in claim 1 wherein X is S.

3. The photographic element recited in claim 2 wherein $R^1$, $R^2$, $R^3$, and $R^4$ each independently represents H; halogen; alkyl of 1–6 carbons; or $R^1$ and $R^2$, $R^2$ and $R^3$, or $R^3$ and $R^4$ are taken together represent the atoms necessary to complete a six-membered carbocylic ring.

4. The photographic element recited in claim 3 wherein Y is S.

5. The photographic element recited in claim 4 wherein Z is S.

6. The photographic element recited in claim 5 wherein n is an integer of 2–4.

7. The photographic element recited in claim 6 wherein at least one said dye is chosen from the group consisting of

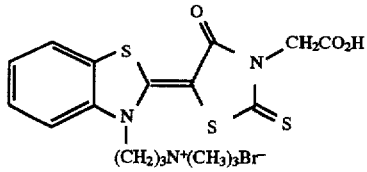

-continued

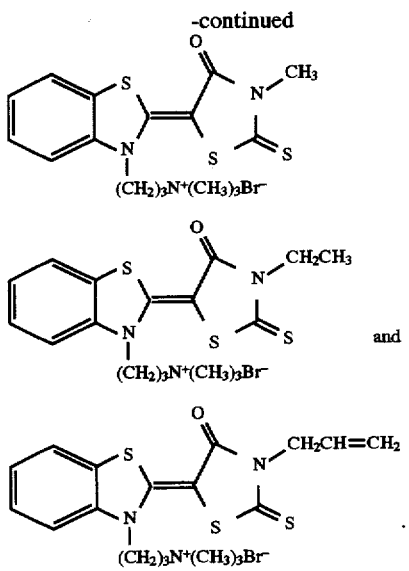

8. The photographic element recited in claim 7 wherein at least one said dye is

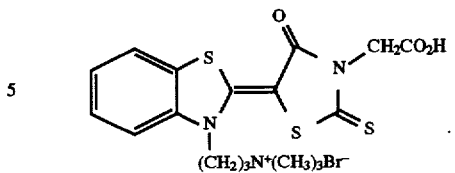

9. The photographic element recited in claim 1 wherein said dye is present in an amount of 10 to 5000 mg of dye per mole of silver.

10. The photographic element recited in claim 9 wherein said dye is present in an amount of 20 to 2000 mg of dye per mole of silver.

11. The photographic element recited in claim 1 wherein said photographic element comprises at least two said hydrophilic colloid layers coated on said support.

12. The photographic element recited in claim 11 wherein said at least two said hydrophilic colloid layers are coated on both sides of said support.

* * * * *